United States Patent
Garcia Molina

(10) Patent No.: US 11,724,060 B2
(45) Date of Patent: Aug. 15, 2023

(54) METHOD AND SYSTEM FOR ENHANCEMENT OF SLOW WAVE ACTIVITY AND PERSONALIZED MEASUREMENT THEREOF

(71) Applicant: KONINKLIJKE PHILIPS N.V., Eindhoven (NL)

(72) Inventor: Gary Nelson Garcia Molina, Madison, WI (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 116 days.

(21) Appl. No.: 17/111,886

(22) Filed: Dec. 4, 2020

(65) Prior Publication Data
US 2021/0170138 A1   Jun. 10, 2021

Related U.S. Application Data

(60) Provisional application No. 62/945,476, filed on Dec. 9, 2019.

(51) Int. Cl.
*A61M 21/00* (2006.01)
*A61B 5/00* (2006.01)
*A61B 5/38* (2021.01)

(52) U.S. Cl.
CPC .............. *A61M 21/00* (2013.01); *A61B 5/38* (2021.01); *A61B 5/4812* (2013.01); *A61B 5/4815* (2013.01); *A61M 2021/0027* (2013.01)

(58) Field of Classification Search
CPC ............ A61M 21/00–02; A61B 5/4806–4815
See application file for complete search history.

(56) References Cited

U.S. PATENT DOCUMENTS

| | | |
|---|---|---|
| 2016/0082222 A1 | 3/2016 | Garcia Molina et al. |
| 2016/0296164 A1* | 10/2016 | Garcia Molina ...... A61B 5/369 |
| 2017/0000970 A1* | 1/2017 | Garcia Molina ..... A61M 21/02 |
| 2018/0256094 A1* | 9/2018 | Russell ............... A61B 5/6824 |
| 2018/0311462 A1* | 11/2018 | Garcia Molina ...... A61B 5/316 |
| 2019/0083028 A1 | 3/2019 | Garcia Molina et al. |

(Continued)

FOREIGN PATENT DOCUMENTS

WO   2018104163 A1   6/2018

OTHER PUBLICATIONS

International Search Report and Written Opinion, International Application No. PCT/EP2020/084564, dated Feb. 18, 2021.

(Continued)

*Primary Examiner* — Thaddeus B Cox

(57) ABSTRACT

The present disclosure pertains to enhancement of slow wave activity and personalized measurement thereof. Sensory stimulation may be delivered to a subject upon detection of slow wave activity of the subject. The system may obtain a baseline model, which includes baseline information describing slow wave activity increases due to sensory stimulation delivered to an age matched population. The system may generate a personalized model based on the baseline information, the sensory stimulation delivered to the subject, and slow wave activity increases due to sensory stimulation delivered to the subject during prior sleep sessions. The system may then provide the subject with personalized measurements relating to the slow wave activity enhancement.

21 Claims, 6 Drawing Sheets

(56) References Cited

U.S. PATENT DOCUMENTS

2019/0192069 A1   6/2019   Garcia Molina et al.
2019/0254591 A1   8/2019   Garcia Molina et al.
2019/0344042 A1   11/2019  Garcia Molina et al.

OTHER PUBLICATIONS

Bellesi, M. et al., "Enhancement of sleep slow waves: underlying mechanisms and practical consequences", Frontiers in Systems Neuroscience, Oct. 28, 2014.
Garcia-Molina, G. et al. (2018) 'Closed-loop system to enhance slow-wave activity', Journal of neural engineering, 15(6), pp. 1-11. doi: 10.1088/1741-2552/aae18f.
Jasper, H. H. (1958) 'The ten-twenty electrode system of the international federation', Electroencephalography and Clinical Neurophysiology, 10(1), pp. 371-375.
Ngo, H.-V. V et al. (2015) 'Driving Sleep Slow Oscillations by Auditory Closed-Loop Stimulation—A Self-Limiting Process', Journal of Neuroscience, 35(17), pp. 6630-6638. doi: 10.1523/JNEUROSCI.3133-14.2015.
Papalambros, N. A. et al. (2017) 'Acoustic enhancement of sleep slow oscillations and concomitant memory improvement in older adults', Frontiers in human neuroscience, 11(March), pp. 1-14. doi: 10.3389/fnhum.2017.00109.
Papalambros, N. A. et al. (2019) 'Acoustic enhancement of sleep slow oscillations in mild cognitive impairment', pp. 1-42. doi: 10.1002/acn3.796.

\* cited by examiner

METHOD AND SYSTEM FOR ENHANCEMENT OF SLOW WAVE ACTIVITY AND PERSONALIZED MEASUREMENT THEREOF

CROSS-REFERENCE TO PRIOR APPLICATIONS

This application claims the benefit of U.S. Provisional Application No. 62/945,476, filed on 9 Dec. 2019. This application is hereby incorporated by reference herein.

BACKGROUND

1. Field

The present disclosure pertains to a system and method for enhancing slow wave activity and providing a personalized measurement thereof.

2. Description of the Related Art

Systems for monitoring sleep and delivering sensory stimulation to subjects during sleep are known. Electroencephalogram (EEG) sensor-based sleep monitoring and sensory stimulation systems are known.

SUMMARY

Systems and methods described herein may provide enhancements to the slow wave activity of a subject and personalized measurements thereof. Accordingly, one or more aspects of the present disclosure relate to a system configured to measure slow wave activity of a subject during a sleep session. The system comprises one or more sensors, one or more sensory stimulators, one or more processors, and/or other components. The one or more sensors are configured to generate output signals conveying information related to brain activity of the subject during the sleep session. The one or more sensory stimulators are configured to provide the sensory stimulation to the subject during the sleep session. The one or more processors are coupled to the one or more sensors and the one or more sensory stimulators. The one or more processors are configured by machine-readable instructions. The one or more processors are configured to control the one or more sensory stimulators based on stimulation parameters.

In some embodiments, the one or more sensors comprise one or more electroencephalogram (EEG) electrodes configured to generate the information related to brain activity. In some embodiments, the one or more processors are further configured to detect deep sleep in the subject. In some embodiments, the one or more processors are configured to determine that the subject has remained in deep sleep for a continuous threshold amount of time during the sleep session. In some embodiments, the one or more processors are further configured to estimate the likelihood of sleep micro-arousals.

In some embodiments, detecting deep sleep comprises causing a deep learning algorithm to be trained based on the information related to the brain activity of the subject, as captured by the EEG electrodes. In some embodiments, based on the output signals, the trained deep learning algorithm may determine periods when the subject is experiencing deep sleep during the sleep session. The trained deep learning algorithm comprises an input layer, an output layer, and one or more intermediate layers between the input layer and the output layer.

In some embodiments, the one or more processors are configured such that, once deep sleep is detected and the likelihood of sleep micro-arousals is below a threshold, the processors apply stimulations to the subject. In some embodiments, the stimulations may be repeating vibrations, constant vibration, repeating light pulses, constant light stimulation, and/or other repeating or constant stimulations. In some embodiments, repeating stimulations are separated from one another by a constant interval. In some embodiments, the intensity of the stimulations is based upon the depth of sleep.

In some embodiments, the one or more processors are configured to detect slow wave activity in the subject during the sleep session. The one or more processors may determine an increase in slow wave activity of the subject throughout the sleep session, where the increase is caused by the sensory stimulation provided to the subject. The increase in slow wave activity is determined based on a baseline model and a personalized model. In some embodiments, the baseline model may describe increases in slow wave activity in a population of subjects (e.g., an age-matched population) as a function of sensory stimulation provided to the population of subjects. In some embodiments, the personalized model may utilize slow wave activity for the subject measured during prior sleep sessions in which the sensory stimulation was provided to the subject, as well as information from the baseline model. In some embodiments, the personalized model may be modified based on the baseline model and the slow wave activity as measured by the one or more sensors during the sleep session.

In some embodiments, the one or more processors may provide personalized measurements to the subject following the sleep session based on the baseline model and the modified personalized model. In some embodiments, the sleep quality feedback may comprise a "boost" calculation, which indicates the sleep quality benefit derived from receiving the stimulations during the sleep sessions. In some embodiments, the boost calculation comprises information about slow wave activity enhancement for the age matched population of subjects and information about slow wave activity enhancement for the subject. In some embodiments, the sleep quality feedback may also comprise a score that accounts for other sleep factors. The sleep quality feedback may combine the score and the boost in order to provide the subject with overall quantitative sleep quality feedback for the sleep session.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
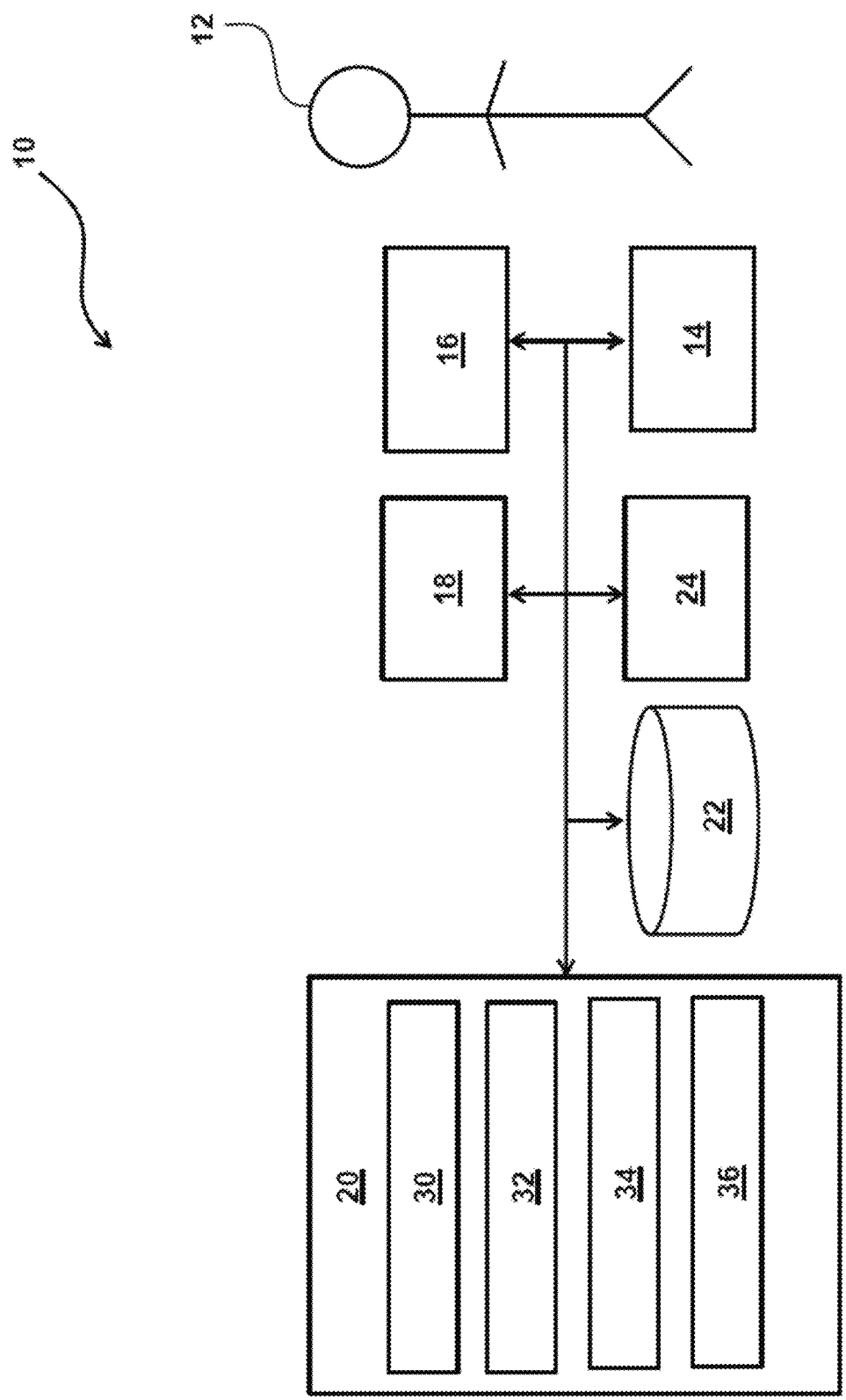
FIG. 1 is a schematic illustration of a system configured to deliver sensory stimulation to a subject during a sleep session, in accordance with one or more embodiments.

As used herein, the singular form of "a", "an", and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled to move as one while maintaining a constant orientation relative to each other.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 configured to measure slow wave activity of a subject 12 during a sleep session. System 10 is configured to measure an increase in slow wave activity of the subject during the sleep session based on a baseline model and a personalized model to provide the subject with sleep quality feedback and/or for other purposes. System 10 is configured such that sensory stimulation, which may include auditory, haptic, light, and/or other stimulation, is delivered during sleep. In some embodiments, the stimulation is only delivered to the subject when processors in system 10 (described below) have determined that subject 12 is in deep sleep and that the likelihood of micro-arousals is low (e.g., below a threshold). In some embodiments, system 10 delivers stimulations to subject 12 (e.g., vibrations and/or light pulses). In some embodiments, the stimulations may be repeating stimulations (e.g., repeating vibrations and/or repeating light pulses) and/or constant stimulations delivered to the subject for the duration of the deep sleep period. As described herein, the one or more processors may adjust the intensity of the stimulations based on the depth of sleep (i.e., as sleep becomes deeper the one or more processors increase the intensity of the stimulations). The one or more processors may then determine an increase in slow wave activity caused by the sensory stimulations provided to subject 12. The increase may be based upon the baseline model and the personalized model. In some embodiments, the baseline model describes increases in slow wave activity in an age matched population of subjects as a function of sensory stimulation provided to the age matched population of subjects. In some embodiments, the personalized model utilizes and/or is based on slow wave activity for subject 12 measured during prior sleep sessions in which the sensory stimulation was provided to subject 12.

In some embodiments, the one or more processors may modify the personalized model based on the baseline model and the slow wave activity as measured by the one or more sensors during the sleep session. The one or more processors may then use the modified personalized model subsequently (e.g., later in the sleep session and/or in subsequent sleep sessions).

Providing accurate sleep quality feedback to subject 12 which accounts for enhancement due to sensory stimulation is important to subject 12's understanding of their sleep quality. The use of sleep quality information for populations of subject (e.g., age-matched populations) may be accurate for certain subjects but may fail to accurately represent sleep quality for other subjects. The combination of a baseline model (i.e., accounting for sleep information for the age-matched population) with a personalized model (i.e., accounting for sleep information for the subject) allows for more accurate sleep quality feedback for different subjects. The use of a baseline model additionally removes (or at least reduces) the need for a calibration period in which the system learns the habits of the subject and does not provide sleep quality feedback. As shown in FIG. 1, system 10 includes one or more of a sensor 14, a sensory stimulator 16, external resources 18, a processor 20, electronic storage 22, a subject interface 24, and/or other components. These components are further described below.

Sensor 14 is configured to generate output signals conveying information related to sleep stages of subject 12 during a sleep session. The output signals conveying information related to sleep stages of subject 12 may include information related to brain activity in subject 12. As such, sensor 14 is configured to generate output signals conveying information related to brain activity. In some embodiments, sensor 14 is configured to generate output signals conveying information related to stimulation provided to subject 12 during sleep sessions. In some embodiments, the information in the output signals from sensor 14 is used to control sensory stimulator 16 to provide sensory stimulation to subject 12 (as described below).

Sensor 14 may comprise one or more sensors that generate output signals that convey information related to brain activity in subject 12 directly. For example, sensor 14 may include electroencephalogram (EEG) electrodes configured to detect electrical activity along the scalp of subject 12 resulting from current flows within the brain of subject 12. Sensor 14 may comprise one or more sensors that generate output signals conveying information related to brain activity of subject 12 indirectly. For example, one or more sensors 14 may comprise a heart rate sensor that generates an output based on a heart rate of subject 12 (e.g., sensor 14 may be a heart rate sensor than can be located on the chest of subject 12, and/or be configured as a bracelet on a wrist of subject 12, and/or be located on another limb of subject 12), movement of subject 12 (e.g., sensor 14 may comprise an accelerometer that can be carried on a wearable, such as a bracelet around the wrist and/or ankle of subject 12 such that sleep may be analyzed using actigraphy signals), respiration of subject 12, and/or other characteristics of subject 12.

In some embodiments, sensor 14 may comprise one or more of EEG electrodes, a respiration sensor, a pressure sensor, a vital signs camera, a functional near infra-red sensor (fNIR), a temperature sensor, a microphone and/or other sensors configured to generate output signals related to (e.g., the quantity, frequency, intensity, and/or other characteristics of) the stimulation provided to subject 12, the brain activity of subject 12, and/or other sensors. Although sensor 14 is illustrated at a single location near subject 12, this is not intended to be limiting. Sensor 14 may include sensors disposed in a plurality of locations, such as for example, within (or in communication with) sensory stimulator 16, coupled (in a removable manner) with clothing of subject 12, worn by subject 12 (e.g., as a headband, wristband, etc.), positioned to point at subject 12 while subject 12 sleeps (e.g., a camera that conveys output signals related to movement of subject 12), coupled with a bed and/or other furniture where subject 12 is sleeping, and/or in other locations.

Figure 2:
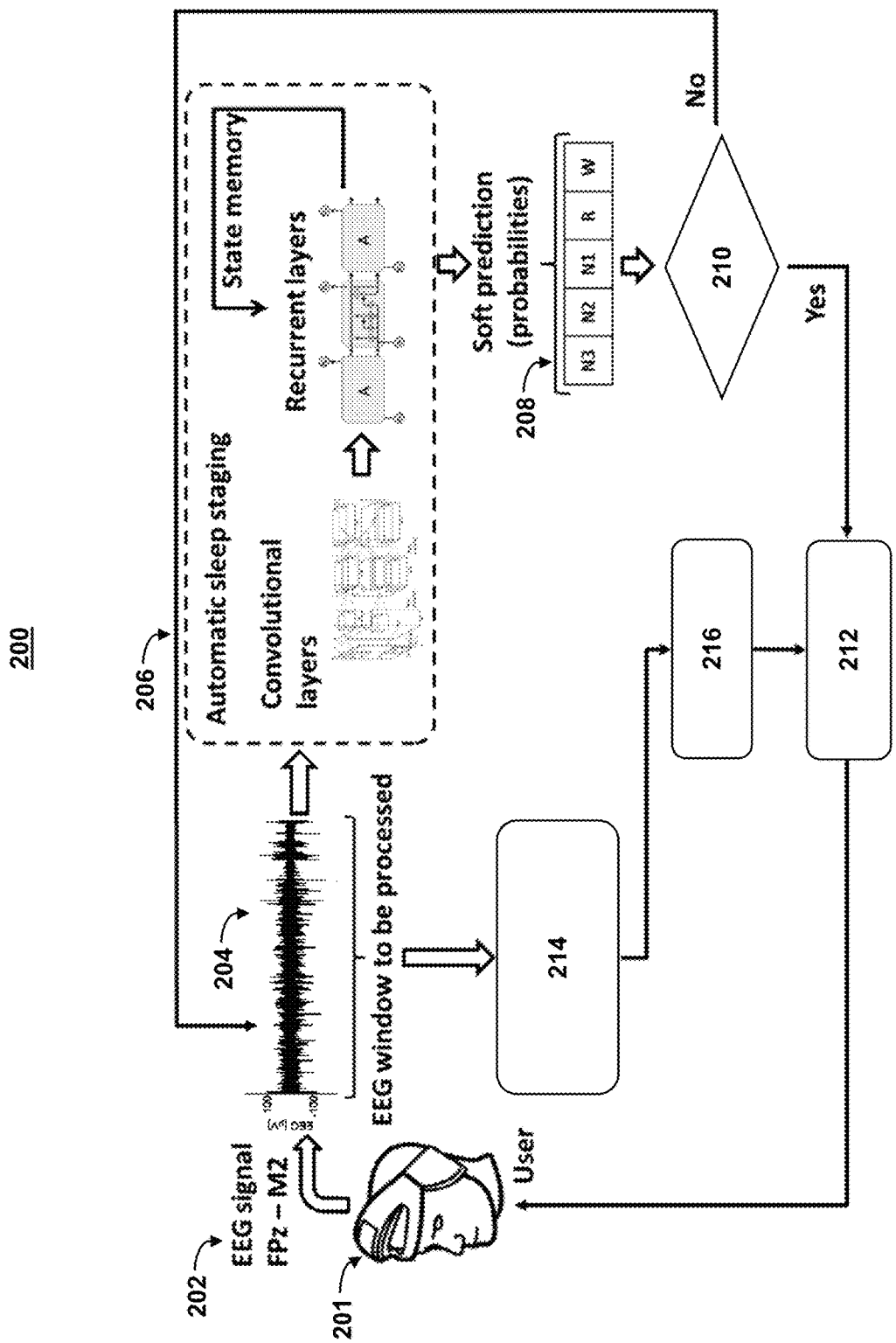
FIG. 2 illustrates several of the operations performed by the system, in accordance with one or more embodiments.

In FIG. 1, sensor 14, sensory stimulator 16, processor 20, electronic storage 22, and subject interface 24 are shown as separate entities. This is not intended to be limiting. Some and/or all of the components of system 10 and/or other components may be grouped into one or more singular devices. For example, these and/or other components may be included in a wearable device 201. In some embodiments, wearable device 201 may be a headset as illustrated in FIG. 2 and/or other garments worn by subject 12. Other garments may include a cap, vest, bracelet, and/or other garment. In some embodiments, wearable device 201 may comprise one or more sensors which may contact the skin of the subject. In some embodiments, wearable device 201 may comprise one or more sensory stimulators, which may provide visual, somatosensory, and or auditory stimulation. For example, wearable device 201 and/or other garments may include, for example, sensing electrodes, a reference electrode, one or more devices associated with an EEG, means to deliver auditory stimulation (e.g., a wired and/or wireless audio device and/or other devices), and one or more audio speakers. In some embodiments, wearable device 201 may comprise means to delivery visual, somatosensory, electric, magnetic, and/or other stimulation to the subject. In this example, the audio speakers may be located in and/or near the ears of subject 12 and/or in other locations. The reference electrode may be located behind the ear of subject 12, and/or in other locations. In this example, the sensing electrodes may be configured to generate output signals conveying information related to brain activity of subject 12, and/or other information. The output signals may be transmitted to a processor (e.g., processor 20 shown in FIG. 1), a computing device (e.g., a bedside laptop) which may or may not include the processor, and/or other devices wirelessly and/or via wires. In some embodiments, the processor may be in electric communication with the one or more sensors and the one or more sensory stimulators. In some embodiments, the processor may be located within wearable device 201 and/or located externally. In this example, acoustic stimulation may be delivered to subject 12 via the wireless audio device and/or speakers. In this example, the sensing electrodes, the reference electrode, and the EEG devices may be represented, for example, by sensor 14 in FIG. 1. The wireless audio device and the speakers may be represented, for example, by sensory stimulator 16 shown in FIG. 1. In this example, a computing device may include processor 20, electronic storage 22, subject interface 24, and/or other components of system 10 shown in FIG. 1.

Stimulator 16 is configured to provide sensory stimulation to subject 12. Sensory stimulator 16 is configured to provide auditory, visual, somatosensory, electric, magnetic, and/or sensory stimulation to subject 12 prior to a sleep session, during a sleep session, and/or at other times. In some embodiments, a sleep session may comprise any period of time when subject 12 is sleeping and/or attempting to sleep. Sleep sessions may include nights of sleep, naps, and/or other sleeps sessions. For example, sensory stimulator 16 may be configured to provide stimuli to subject 12 during a sleep session to enhance EEG signals during deep sleep in subject 12, and/or for other purposes.

Sensory stimulator 16 is configured to affect deep sleep in subject 12 through non-invasive brain stimulation and/or other methods. Sensory stimulator 16 may be configured to affect deep sleep through non-invasive brain stimulation using auditory, electric, magnetic, visual, somatosensory, and/or other sensory stimuli. The auditory, electric, magnetic, visual, somatosensory, and/or other sensory stimulation may include auditory stimulation, visual stimulation, somatosensory stimulation, electrical stimulation, magnetic stimulation, a combination of different types of stimulation, and/or other stimulation. The auditory, electric, magnetic, visual, somatosensory, and/or other sensory stimuli include odors, sounds, visual stimulation, touches, tastes, somatosensory stimulation, haptic, electrical, magnetic, and/or other stimuli. The sensory stimulation may have an intensity, a timing, and/or other characteristics. For example, acoustic tones may be provided to subject 12 to affect deep sleep in subject 12. The acoustic tones may include one or more series of tones of a determined length (e.g., less than a decisecond, 50 milliseconds, etc.) separated from each other by an interval (e.g., one second). The volume (i.e., the intensity) of individual tones may be modulated based on depth of sleep and/or other factors (as described herein). In some embodiments, the initial volume may be imperceptible, set to a default volume, and/or set by the subject via a subject interface (e.g., 24, as shown in FIG. 1). The length of individual tones (e.g., the timing), the interval between tones, the pitch of the tones, and the type of tone may also be adjusted. This example is not intended to be limiting, and the stimulation parameters may vary.

Examples of sensory stimulator 16 may include one or more of a sound generator, a speaker, a music player, a tone generator, a vibrator (such as a piezoelectric member, for example) to deliver vibratory stimulation, a coil generating a magnetic field to directly stimulate the brain's cortex, one or more light generators or lamps, a fragrance dispenser, and/or other devices. In some embodiments, sensory stimulator 16 is configured to adjust the intensity, timing, and/or other parameters of the stimulation provided to subject 12 (e.g., as described below).

External resources 18 include sources of information (e.g., databases, websites, etc.), external entities participating with system 10 (e.g., one or more the external sleep monitoring devices, a medical records system of a health care provider, etc.), and/or other resources. In some embodiments, external resources 18 include components that facilitate communication of information, one or more servers outside of system 10, a network (e.g., the internet), electronic storage, equipment related to Wi-Fi technology, equipment related to Bluetooth® technology, data entry devices, sensors, scanners, computing devices associated with individual subjects, and/or other resources. In some implementations, some or all of the functionality attributed herein to external resources 18 may be provided by resources included in system 10. External resources 18 may be configured to communicate with processor 20, subject interface 24, sensor 14, electronic storage 22, sensory stimulator 16, and/or other components of system 10 via wired and/or wireless connections, via a network (e.g., a local area network and/or the internet), via cellular technology, via Wi-Fi technology, and/or via other resources.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16, subject interface 24, etc.), or processor 20 may represent processing functionality of a plurality of devices operating in coordination. In some embodiments, processor 20 may be and/or be included in a computing device such as a desktop computer, a laptop computer, a smartphone, a tablet computer, a server, and/or other computing devices. Such computing devices may run one or more electronic applications having graphical subject interfaces configured to facilitate subject interaction with system 10.

As shown in FIG. 1, processor 20 is configured to execute one or more computer program components. The computer program components may comprise software programs and/or algorithms coded and/or otherwise embedded in processor 20, for example. The one or more computer program components may comprise one or more of an information component 30, a model component 32, a control component 34, a modulation component 36, and/or other components. Processor 20 may be configured to execute components 30, 32, 34, and/or 36 by software; hardware; firmware; some combination of software, hardware, and/or firmware; and/or other mechanisms for configuring processing capabilities on processor 20.

It should be appreciated that although components 30, 32, 34, and 36 are illustrated in FIG. 1 as being co-located within a single processing unit, in embodiments in which processor 20 comprises multiple processing units, one or more of components 30, 32, 34, and/or 36 may be located remotely from the other components. The description of the functionality provided by the different components 30, 32, 34, and/or 36 described below is for illustrative purposes, and is not intended to be limiting, as any of components 30, 32, 34, and/or 36 may provide more or less functionality than is described. For example, one or more of components 30, 32, 34, and/or 36 may be eliminated, and some or all of its functionality may be provided by other components 30, 32, 34, and/or 36. As another example, processor 20 may be configured to execute one or more additional components that may perform some or all of the functionality attributed below to one of components 30, 32, 34, and/or 36.

Information component 30 is configured to determine one or more brain activity parameters of subject 12, and/or other information. The brain activity parameters are determined based on the output signals from sensor 14 and/or other information. The brain activity parameters indicate depth of sleep in subject 12. In some embodiments, the information in the output signals related to brain activity indicates sleep depth over time. In some embodiments, the information indicating sleep depth over time is or includes information related to deep sleep in subject 12.

In some embodiments, the information indicating sleep depth over time may be indicative of other sleep stages of subject 12. For example, the sleep stages of subject 12 may be associated with deep sleep, rapid eye movement (REM) sleep, and/or other sleep. Deep sleep may be stage N3, and/or other deep sleep stages. In some embodiments, the sleep stages of subject 12 may be one or more of stage S1, S2, S3, or S4. In some embodiments, NREM stage 2 and/or 3 (and/or S3 and/or S4) may be slow wave (e.g., deep) sleep.

In some embodiments, the information that indicates sleep depth over time is and/or is related to one or more additional brain activity parameters.

In some embodiments, the information related to brain activity that indicates sleep depth over time is and/or includes EEG information and/or other information generated during sleep sessions of subject 12 and/or at other times. In some embodiments, brain activity parameters may be determined based on the EEG information and/or other information. In some embodiments, the brain activity parameters may be determined by information component 30 and/or other components of system 10. In some embodiments, the brain activity parameters may be previously determined and be part of the historical sleep stage information obtained from external resources 18 (described below). In some embodiments, the one or more brain activity parameters are and/or are related to a frequency, amplitude, phase, presence of specific sleep patterns such as eye movements, ponto-geniculo-occipital (PGO) wave, slow wave, and/or other characteristics of an EEG signal. In some embodiments, the one or more brain activity parameters are determined based on the frequency, amplitude, and/or other characteristics of the EEG signal. In some embodiments, the determined brain activity parameters and/or the characteristics of the EEG may be and/or indicate sleep stages that correspond to the deep sleep stage described above.

Information component 30 is configured to obtain historical sleep stage information. In some embodiments, the historical sleep stage information is for subject 1 and/or other subjects. The historical sleep stage information is related to brain activity, and/or other physiological of the population of subjects and/or subject 12 that indicates sleep stages over time during previous sleep sessions of the population of subjects and/or subject 12. The historical sleep stage information is related to sleep stages and/or other brain parameters of the population of subjects and/or subject 12 during corresponding sleep sessions, and/or other information.

In some embodiments, information component 30 is configured to obtain the historical sleep stage information electronically from external resources 18, electronic storage 22, and/or other sources of information. In some embodiments, obtaining the historical sleep stage information electronically from external resources 18, electronic storage 22, and/or other sources of information comprises querying one more databases and/or servers; uploading information and/or downloading information, facilitating subject input, sending and/or receiving emails, sending and/or receiving text messages, and/or sending and/or receiving other communications, and/or other obtaining operations. In some embodiments, information component 30 is configured to aggregate information from various sources (e.g., one or more of the external resources 18 described above, electronic storage 22, etc.), arrange the information in one or more electronic databases (e.g., electronic storage 22, and/or other electronic databases), normalize the information based on one or more features of the historical sleep stage information (e.g., duration of sleep sessions, number of sleep sessions, number of sleep disruptions, duration of various sleep stages, and/or sleep time regularity etc.) and/or perform other operations.

Model component 32 is configured such that a trained deep learning algorithm and/or any other supervised machine deep learning algorithms are caused to detect deep sleep in subject 12. In some embodiments, this may be and/or include determining periods when subject 12 is experiencing deep sleep during the sleep session and/or other operations. The determined deep sleep, and/or timing, indicates whether subject 12 is in deep sleep for stimulation and/or other information. By way of a non-limiting example, a trained deep learning algorithm may be caused to determine deep sleep stages and/or timing of the deep sleep stages for the subject based on the output signals (e.g., using the information in the output signals as input for the model) and/or other information. In some embodiments, model component 32 is configured to provide the information in the output signals to the deep learning algorithm in temporal sets that correspond to individual periods during the sleep session. In some embodiments, model component 32 is configured to cause the trained deep learning algorithm to output the determined sleep stages of deep sleep for subject 12 during the sleep session based on the temporal sets of information. (The functionality of model component 32 is further discussed below relative to FIG. 2-3.)

As an example, deep learning algorithms may be a deep neural network. A deep neural network may be based on a large collection of neural units (or artificial neurons). Deep learning algorithms may loosely mimic the manner in which a biological brain works (e.g., via large clusters of biological neurons connected by axons). Each neural unit of a deep learning algorithm may be connected with many other neural units of the deep learning algorithm. Such connections can be enforcing or inhibitory in their effect on the activation state of connected neural units. In some embodiments, each individual neural unit may have a summation function that combines the values of all its inputs together. In some embodiments, each connection (or the neural unit itself) may have a threshold function such that a signal must surpass the threshold before it is allowed to propagate to other neural units. These deep learning algorithm systems may be self-learning and trained, rather than explicitly programmed, and can perform significantly better in certain areas of problem solving, as compared to traditional computer programs. In some embodiments, deep learning algorithms may include multiple layers (e.g., where a signal path traverses from front layers to back layers). In some embodiments, back propagation techniques may be utilized by the deep learning algorithms, where forward stimulation is used to reset weights on the "front" neural units. In some embodiments, stimulation and inhibition for deep learning algorithms may be more free flowing, with connections interacting in a more chaotic and complex fashion.

As described above, a trained deep neural network may comprise one or more intermediate or hidden layers. The intermediate layers of the trained deep neural network include one or more convolutional layers, one or more recurrent layers, and/or other layers of the trained deep learning algorithm. Individual intermediate layers receive information from another layer as input and generate corresponding outputs. The detected sleep stages of deep sleep are generated based on the information in the output signals from sensor 14 as processed by the layers of the deep learning algorithm.

Control component 34 is configured to control stimulator 16 to provide stimulation to subject 12 during sleep and/or at other times. Control component 34 is configured to cause sensory stimulator 16 to provide the sensory stimulation to subject 12 during deep sleep to affect deep sleep in subject 12 during a sleep session. Control component 34 is configured to cause sensory stimulator 16 to provide sensory stimulation to subject 12 based on a detected deep sleep stage (e.g., the output from model component 32) and/or other information. Control component 34 is configured to cause sensory stimulator 16 to provide the sensory stimulation to subject 12 based on the detected deep sleep stage and/or other information over time during the sleep session. Control component 34 is configured to cause sensory stimulator 16 to provide sensory stimulation to subject 12 responsive to subject 12 being in, or likely being in, deep sleep for stimulation. For example, control component 34 is configured such that controlling one or more sensory stimulators 16 to provide the sensory stimulation to subject 12 during the deep sleep to affect the deep sleep in subject 12 during the sleep session comprises: determining the periods when subject 12 is experiencing deep sleep, causing one or more sensory stimulators 16 to provide the sensory stimulation to subject 12 during the periods when subject 12 is experiencing deep sleep, and/or causing one or more sensory stimulators 16 to modulate (e.g., as described herein), an amount, a timing, and/or intensity of the sensory stimulation provided to subject 12 based on the one or more values of the one or more intermediate layers. In some embodiments, stimulators 16 are controlled by control component 34 to affect deep sleep through (e.g., peripheral auditory, magnetic, electrical, and/or other) stimulation delivered during deep sleep (as described herein).

In some embodiments, control component 34 is configured to control sensory stimulator 16 to deliver sensory stimulation to subject 12 responsive to model component 32 determining that subject 12 has remained in deep sleep for a continuous threshold amount of time during the sleep session. For example, model component 32 and/or control component 34 may be configured such that on detection of deep sleep, model component 32 starts a (physical or virtual) timer configured to track the time subject 12 spends in deep sleep. Control component 34 is configured to deliver auditory stimulation responsive to the duration that subject 12 spends in continuous deep sleep breaching a predefined duration threshold. In some embodiments, the predefined duration threshold is determined at manufacture of system 10 and/or at other times. In some embodiments, the predefined duration threshold is determined based on information from previous sleep sessions of subject 12 and/or subjects demographically similar to subject 12 (e.g., as described above). In some embodiments, the predefined duration threshold is adjustable via subject interface 24 and/or other adjustment mechanisms.

In some embodiments, the predefined deep sleep duration threshold may be one minute and/or other durations, for example. By way of a non-limiting example, control component 34 may be configured such that auditory stimulation starts once a minute of continuous deep sleep in subject 12 is detected. In some embodiments, once the stimulation begins, control component 34 is configured to control stimulation parameters of the stimulation. Upon detection of a sleep stage transition (e.g., from deep sleep to some other sleep stage), control component 34 is configured to stop stimulation. Modulation component 36 is configured to cause sensory stimulator 16 to modulate an amount, a timing, and/or intensity of the sensory stimulation. Modulation component 36 is configured to cause sensory stimulator 16 to modulate the amount, timing, and/or intensity of the sensory stimulation based on the brain activity parameters, values output from the intermediate layers of the trained deep learning algorithm, and/or other information. As an example, sensory stimulator 16 is caused to modulate the timing and/or intensity of the sensory stimulation based on the brain activity parameters, the values output from the convolutional layers, the values output from the recurrent layers, and/or other information. For example, modulation component 36 may be configured such that sensory stimulation is delivered with an intensity that is proportional to a predicted probability value (e.g., an output from an intermediate layer of a deep learning algorithm) of a particular sleep stage (e.g., deep sleep). In this example, the higher the probability of deep sleep, the more likely the stimulation continues. If sleep micro-arousals are detected and the sleep stage remains in deep sleep, modulation component 36 may be configured such that the intensity of the stimulation is decreased (by for instance five dBs) responsive to individual micro-arousal detections.

By way of a non-limiting example, FIG. 2 illustrates several of the operations performed by system 10 and described above. In the example shown in system 200 of FIG. 2, an EEG signal 202 is processed and/or otherwise provided (e.g., by information component 30 and model component 32 shown in FIG. 1) to a deep learning algorithm 206 in temporal windows 204. Deep learning algorithm 206 detects sleep stages (e.g., N3, N2, N1, REM, and wakefulness). Determination 210 indicates whether the subject is in deep (N3) sleep. Deep learning algorithm 206 may determine the sleep stage of the subject using methods described in the publication "Recurrent Deep Neural Networks for Real-Time Sleep Stage Classification From Single Channel EEG." *Frontiers in Computational Neuroscience.* Bresch, E., Großekathöfer, U., and Garcia-Molina, G. (2018), which is hereby incorporated by reference in its entirety.

As shown in FIG. 2, deep learning algorithm 206 outputs soft prediction probabilities 208. Soft prediction probabilities 208 are prediction probabilities for individual sleep stages. The set of soft prediction probabilities 208 constitute a so-called soft decision vector, which may be translated into a hard decision by determining which sleep stage is associated with a highest probability value (in a continuum of possible values) relative to other sleep stages. These soft decisions make it possible for system 10 to consider different possible sleep states on a continuum rather than being forced to decide which discrete sleep stage "bucket" particular EEG information fits into (as in prior art systems). The terms "soft" and "hard" are not intended to be limiting but may be helpful to use to describe the operations performed by the system. For example, the term "soft output" may be used, because at this stage, any decision is possible. Indeed, the final decision could depend on post-processing of the soft outputs, for example.

Determination 210 indicates whether deep sleep is detected. If deep sleep is not detected at determination 210, system 200 returns to processing EEG signal 202 in temporal window 204 by deep learning algorithm 206. If deep sleep is detected at determination 210, the one or more sensory stimulators apply sensory stimulation 212 to the subject. As described above, the sensory stimulation may be repeating stimulations (e.g., vibrations, light pulses, etc.) and/or constant stimulations. Repeating stimulations may be separated from one another be a constant interval, and the intensity (i.e., volume, brightness, etc.) of the stimulations may vary based on the depth of sleep. These parameters (e.g., volume and timing 216 and/or other parameters) are calculated based on features 214 of the EEG. For example, features 214 of the EEG may indicate that the subject has been in deep sleep for a threshold period of time and that the likelihood of microarousals is low. The one or more sensory stimulators may then increase the volume as the depth of sleep increases (e.g., increased slow wave activity). In some embodiments, the increase in volume may be proportional to the depth of sleep or may otherwise correspond to the depth of sleep.

Figure 3:
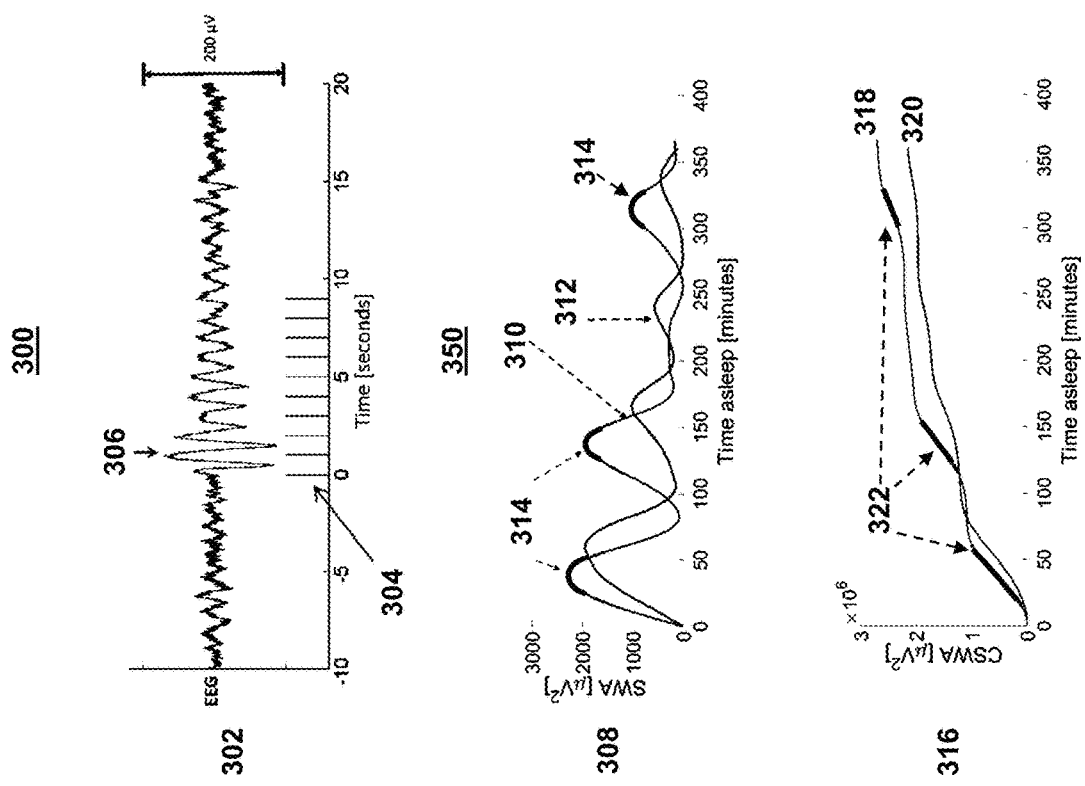
FIG. 3 illustrates slow wave activity enhancement for a subject during a sleep session, in accordance with one or more embodiments.

FIG. 3 illustrates slow wave activity enhancement for a subject during a sleep session. Example 300 shows the effect of sensory stimulations 304 on slow wave activity 306 of the subject. Slow wave activity 306 in graph 302 has a relatively constant amplitude until time zero, when sensory stimulation 304 is applied. Once sensory stimulation 304 is applied, the amplitude of the EEG signal for slow wave activity 306 increases. In example 300, ten stimulations are applied with a constant one-second interval separating the stimulations. In some embodiments, the stimulations may be 50 milliseconds in length and may have an intensity (e.g., volume, brightness, etc.) that is adjusted based on the depth of sleep. The duration, timing, intensity, and other factors are not limited to example 300 and may vary. In addition, example 300 depicts ten stimulations followed by a period of no stimulations. In some embodiments, the sensory stimulators may cease providing sensory stimulation if the subject exits deep sleep and/or if micro-arousals are detected. In some embodiments, if the subject remains in deep sleep and no micro-arousals are detected, the repeating and/or constant stimulations may continue to be delivered to the subject.

Example 350 shows slow wave activity in a subject during a sleep session with sensory stimulation as compared to slow wave activity in the subject during a sleep session without sensory stimulation. In graph 308, stimulated slow wave activity 310 is enhanced at the tone locations 314, i.e., the largest increases in slow wave activity occur at tone locations 314. Additionally, unstimulated slow wave activity 312 is overall lower than stimulated slow wave activity 310. Graph 316 shows cumulative slow wave activity information for the subject across the same range of times as graph 308. Tone locations 322 align temporally with tone locations 314. As shown in graph 316, cumulative stimulated slow wave activity 318 increases at tone locations 322. Cumulative stimulated slow wave activity 318 is overall greater than cumulative unstimulated slow wave activity 320.

Returning to FIG. 1, model component 32 is configured such that both the values output from convolutional layers, and the soft decision value outputs, are vectors comprising continuous values as opposed to discrete values such as sleep stages. Consequently, convolutional and recurrent (soft decision) value outputs are available to be used by system 10 to modulate the volume of the stimulation when the deep learning algorithm detects occurrences of deep sleep. In addition, as described herein, parameters determined (e.g., by information component 30 shown in FIG. 1) based on the raw sensor output signals (e.g., EEG signals) can be used to modulate stimulation settings.

As described above, modulation component 36 is configured to cause sensory stimulator 16 to modulate an amount, timing, and/or intensity of the sensory stimulation. Modulation component 36 is configured to cause sensory stimulator to modulate the amount, timing, and/or intensity of the sensory stimulation based on the one or more brain activity and/or other parameters, values output from the convolutional and/or recurrent layers of the trained deep learning algorithm, and/or other information. As an example, the interval of auditory stimulation provided to subject 12 may be adjusted and/or otherwise controlled (e.g., modulated) based on value outputs from the deep learning algorithm such as convolutional layer value outputs and recurrent layer value outputs (e.g., sleep stage (soft) prediction probabilities). In some embodiments, modulation component 36 is configured to cause one or more sensory stimulators 16 to modulate the amount, timing, and/or intensity of the sensory stimulation, wherein the modulation comprises adjusting the interval, the stimulation intensity, and/or the stimulation frequency, responsive to an indication subject 12 is experiencing one or more micro-arousals.

In some embodiments, modulation component 36 is configured to modulate the sensory stimulation based on the brain activity and/or other parameters alone, which may be determined based on the output signals from sensors 14 (e.g., based on a raw EEG signal). In these embodiments, the output of a deep learning algorithm (and/or other machine learning models) continues to be used to detect sleep stages (e.g., as described above). However, the stimulation intensity and timing are instead modulated based on brain activity and/or other parameters or properties determined based on the sensor output signals. In some embodiments, the information in, or determined based on, the sensor output signals can also be combined with intermediate outputs of the network such as output of the convolution layers or the final outputs (soft stages) to modulate intensity and timing (e.g., as described herein).

Figure 4:
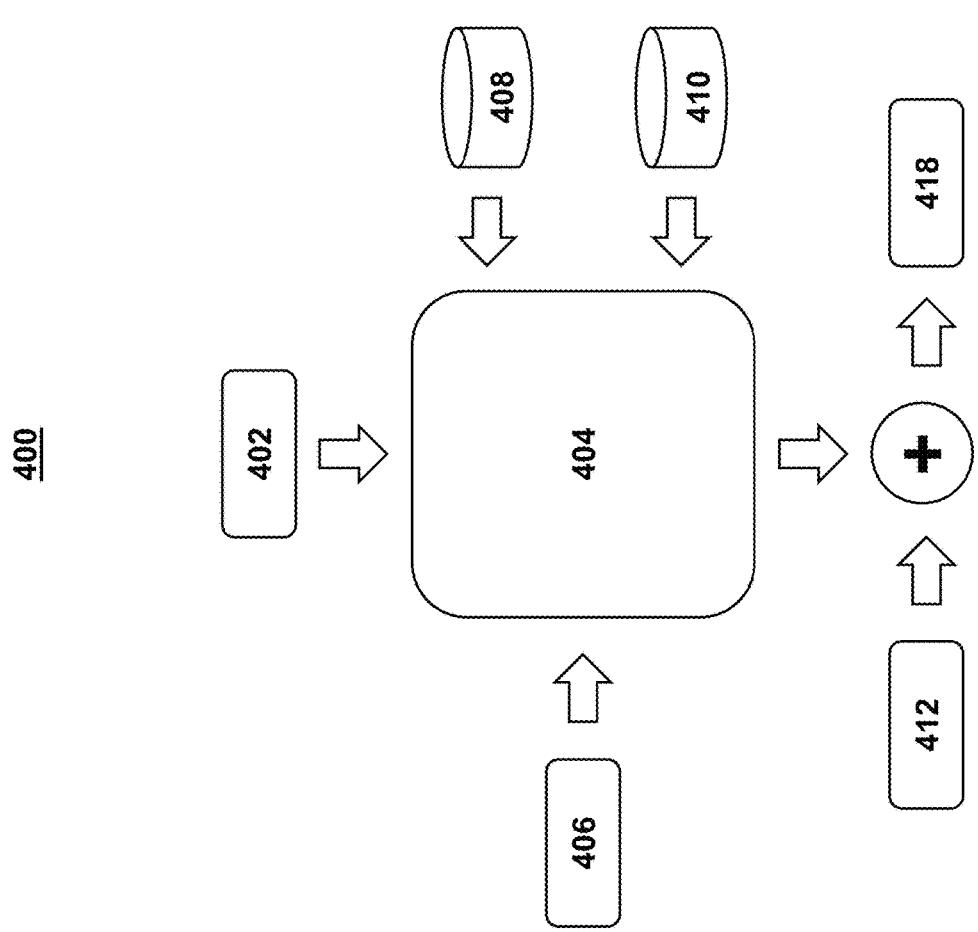
FIG. 4 illustrates contributing factors for sleep quality feedback, in accordance with one or more embodiments.

FIG. 4 illustrates contributing factors for sleep quality feedback. Quantitative sleep quality feedback is useful the subject (e.g., 12, as shown in FIG. 1) to assess the quality of their sleep and factors which detract from and/or improve sleep quality. Sleep quality feedback may be provided as a part of a sleep enhancement system (e.g., such as the SmartSleep system) and/or separately. In some embodiments, the contributing factors may include sleep architecture factors and cumulative slow wave activity throughout the sleep session. The factors are combined to produce a sleep quality score for the sleep session.

System 400 illustrates one method of combining relevant factors to calculate a sleep quality score. System 400 may begin with score 402. Score 402 may be an initial score (e.g., 100%) which represents a perfect score. In some embodiments, score 402 represents the sleep quality of a perfect night of sleep (e.g., having a sufficiently long duration, with no disruptions, etc.). Other inputs include subject history database 408 and reference database 410. Subject history database 408 may provide information such as regular bedtimes and wakeup times, as well as typical slow wave activity of the subject (e.g., 12, as shown in FIG. 1) across sleep sessions. Reference database 410 may store and/or provide information related to matched populations (e.g., such as gender-matched populations, age-matched populations, and/or other matched populations). In some embodiments, the information related to increases in slow wave activity in the age matched population of subjects is received by reference database 410 and/or is preprogrammed within reference database 410. Stored information related to the matched populations may include typical sleep architecture information for the matched populations (e.g., bedtimes and wakeup times, slow wave activity of the populations across sleep sessions, and/or other information). In addition, sleep architecture metrics 406 for the subject are also factored into the sleep feedback calculation. Sleep architecture metrics may include information about the slow wave activity, cumulative slow wave activity, duration, disruptions, and regularity of the subject's sleep session and/or sessions. In some embodiments, sleep architecture metrics 406 may be based upon EEG signals measured by one or more sensors (e.g., 14, as shown in FIG. 1).

In some embodiments, system 400 may use the information received from sleep architecture metrics 406, subject history database 408, and reference database 410 to determine deductions 404. In some embodiments, deductions 404 are subtracted from sleep score 402. Deductions 404 may be features identified from sleep architecture metrics 406, subject history database 408, and reference database 410 which have a negative impact on sleep quality. Deductions 404 may include total sleep duration, wake after sleep onset, sleep onset latency, number of sleep disruptions, deep sleep duration, REM sleep duration, bedtime regularity, wakeup time regularity, and/or other factors. In some embodiments, each factor has a pre-defined value and/or range of values that is subtracted from sleep score 402 if identified within the subject's sleep session and/or sessions. In some embodiments, the subject may input values and/or ranges of values for deductions 404 via a subject interface (e.g., 24, as shown in FIG. 1).

In some embodiments, once deductions 404 have been subtracted from score 402, the resulting score is combined with a boost calculation 412. The boost calculation 412 is representative of the improvement to sleep quality of the sleep session and/or sessions that resulted from the sensory stimulations provided to the subject (e.g., 12, as shown in FIG. 1). For example, boost calculation 412 may represent increases in cumulative slow wave activity in the subject during the sleep session and/or sessions as a result of the stimulation provided to the subject via sensory stimulators (e.g., 16, as shown in FIG. 1). In some embodiments, boost calculation 412 may be based upon a matched population (e.g., age-matched, gender-matched, BMI-matched, and/or other matched population). In some embodiments, boost calculation 412 may be based upon slow wave activity information that is specific to the subject. In some embodiments, boost calculation 412 may be based upon another source of sleep enhancement information. In some embodiments, boost calculation 412 may be based upon any combination of the aforementioned sources. In some embodiments, the one or more processors (e.g., 20, as shown in FIG. 1), may convert the slow wave activity information into a boost score (e.g., compatible with score 402 and deductions 404). The one or more processors may then combine boost calculation 412 with the combination of score 402 and deductions 404. The resulting score, sleep quality feedback score 418, represents negative effects on the subject's sleep session and/or sessions as well as the positive effects of the sensory stimulation (e.g., via sensory stimulators 16).

Boost calculation 412 may be calculated using various techniques. These techniques may alter the accuracy of boost calculation 412 and resulting sleep quality feedback score 418. A technique which combines several sources of sleep quality information, as described in FIG. 5, may provide increased accuracy of sleep quality feedback scores for certain subjects.

Figure 5:
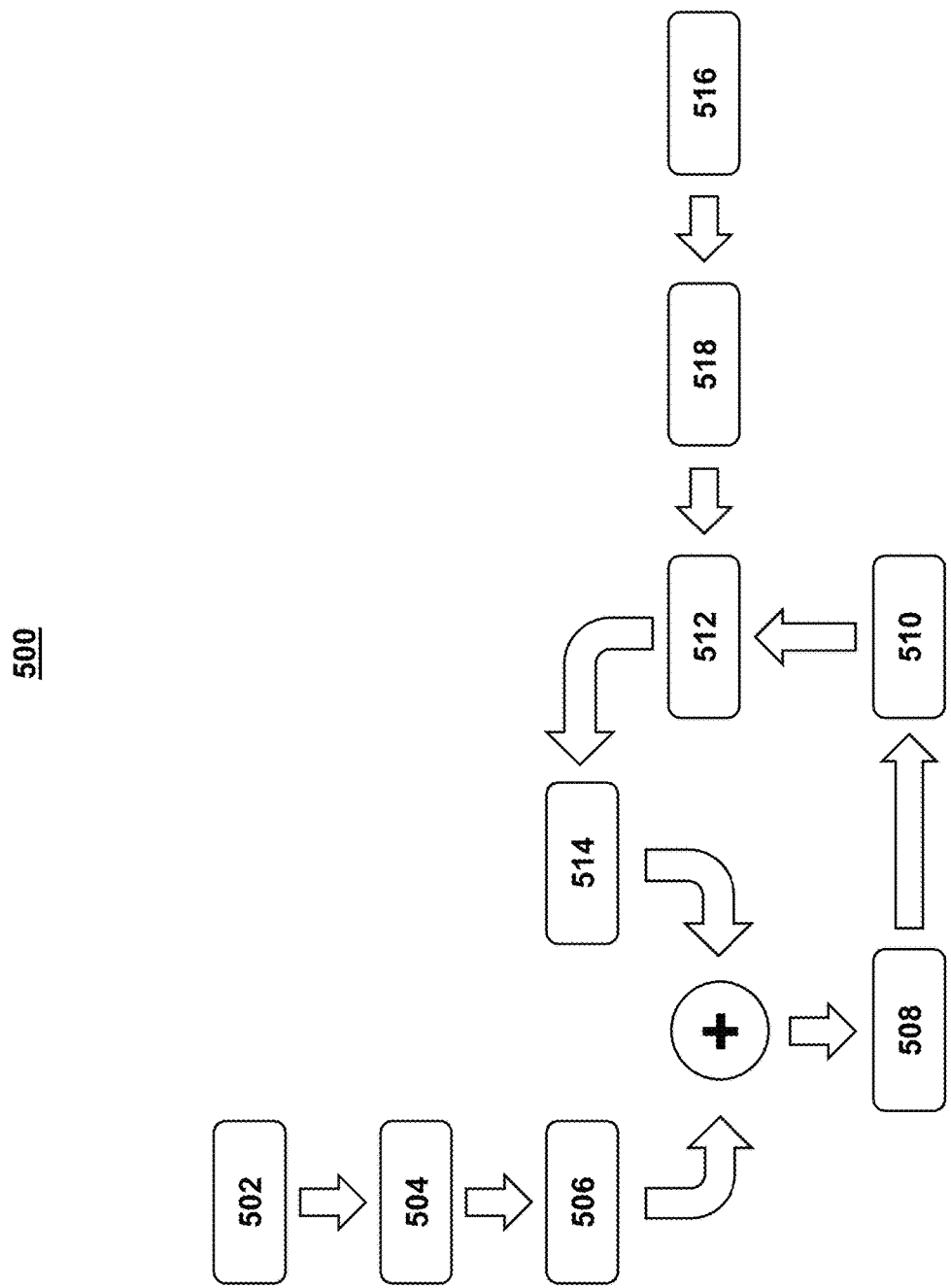
FIG. 5 illustrates components of a sleep boost calculation, in accordance with one or more embodiments.

FIG. 5 illustrates components of a sleep boost calculation (e.g., boost calculation 412, as shown in FIG. 4). System 500 shows the combination of a baseline model 504 (i.e., matched population sleep information) and a personalized model 510 (i.e., specific to the subject). In some embodiments, baseline model 504 may comprise information about increases in the slow wave activity throughout deep sleep for different age ranges as a function of sensory stimulation provided to the age matched population of subjects. In some embodiments, the information related to increases in slow wave activity in the age matched population of subjects is received or preprogrammed. The system may select the age group that corresponds to the subject (e.g., 12, as shown in FIG. 1) and may use the associated slow wave activity information for the age group as an approximation of the slow wave activity of the subject during the sleep session. An example of using data from an age matched population of subject to determine an increase in slow wave activity in a subject is described in European Pat. App. Pub. No. 3457411, which is hereby incorporated by reference in its entirety. Baseline model 504 may utilize inputs 502, which may include cumulative slow wave activity information for a sleep session for the selected age group, a number of stimulations delivered to the subject during the sleep session and/or a duration of stimulations delivered to the subject during the sleep session, deep sleep information (e.g., depth of sleep, duration of deep sleep, and/or other deep sleep factors), and/or additional inputs. The one or more processors (e.g., 20, as shown in FIG. 1), may combine inputs 502 to produce a slow wave activity enhancement value for the sleep session according to the baseline model. This slow wave activity enhancement value may be baseline boost 506. In some embodiments, baseline boost 506 may be used as the value for boost calculation 412. In some embodiments, baseline boost 506 may be combined with a slow wave activity enhancement value for the sleep session according to the personalized model in order to calculate boost calculation 412.

In some embodiments, a threshold amount of sleep data for the subject (e.g., 12, as shown in FIG. 1) is needed before the system can create personalized model 512. Therefore, system 500 may use initial model 518 to collect and analyze the subject's initial sleep data. For example, initial model 518 may utilize inputs 516 which include data for a number of sleep sessions. In some embodiments, the number of sleep sessions comprising the data for inputs 516 may be the first several sleep sessions (e.g., the first seven, ten, or another number of sleep sessions) for which the subject is receiving sensory stimulation. In some embodiments, the number of initial sleep sessions may vary. In some embodiments, only valid sleep sessions are included in the initial sleep sessions. In some embodiments, if a pre-determined number of valid sleep sessions is exceeded, only the most recent valid sleep sessions are included. In some embodiments, data collected from the initial sleep sessions may comprise cumulative slow wave activity information for the initial sleep sessions and the duration and/or number of stimulations provided to the subject during the initial sleep sessions. This data may be included in inputs 516. Baseline boost 506 may also be included in inputs 516. In some embodiments, initial model 518 may collect inputs 516 until a threshold number of initial sleep sessions is reached, at which time, initial model 518 may generate personalized model 512.

In some embodiments, personalized model 512 may initially utilize the data collected by initial model 518. The data collected by initial model 518 may comprise baseline boost 506, cumulative slow wave activity, stimulation information for the initial sleep sessions, and/or other information (i.e., inputs 516). Personalized model 512 may combine this data to calculate personalized boost 514. In some embodiments, personalized model 512 may use various equations to combine inputs 516 to generate personalized boost 514. In some embodiments, personalized model 512 may use one or more of equations 1 and 2 and/or other equations.

$$\text{Personalized Boost} = \beta_0 + \beta_1 \times \text{Tones} + \beta_2 \times CSWA \quad \text{Equation 1}$$

$$\beta_2 = \frac{\langle \text{Tones}^2 \rangle \times \langle CSWA \times \text{Boost} \rangle - \langle \text{Tones} \times CSWA \rangle \langle \text{Tones} \times \text{Boost} \rangle}{\langle \text{Tones}^2 \rangle \langle CSWA^2 \rangle - \langle \text{Tones} \times CSWA \rangle^2} \quad \text{Equation 2}$$

$$\beta_1 = \frac{\langle CSWA^2 \rangle \times \langle CSWA \times \text{Boost} \rangle - \langle \text{Tones} \times CSWA \rangle \langle CSWA \times \text{Boost} \rangle}{\langle \text{Tones}^2 \rangle \langle CSWA^2 \rangle - \langle \text{Tones} \times CSWA \rangle^2}$$

$$\beta_0 = \langle \text{Boost} \rangle - \beta_1 \times \langle \text{Tones} \rangle - \beta_2 \times \langle CSWA \rangle$$

where:

$$\langle \text{Tones} \rangle = \frac{1}{n} \sum_i^n \text{Tones}_i$$

$$\langle CSWA \rangle = \frac{1}{n} \sum_i^n CSWA_i$$

$$\langle \text{Boost} \rangle = \frac{1}{n} \sum_i^n \text{Boost}_i$$

$$\langle \text{Tones} \times \text{Boost} \rangle = \frac{1}{n} \sum_{i=1}^{n=7} \text{Tones}_i \times \text{Boost}_i$$

$$\langle \text{Tones} \times CSWA \rangle = \frac{1}{n} \sum_{i=1}^{n=7} \text{Tones}_i \times CSWA_i$$

$$\langle CSWA \times \text{Boost} \rangle = \frac{1}{n} \sum_{i=1}^{n=7} CSWA_i \times \text{Boost}_i$$

$$\langle \text{Tones}^2 \rangle = \frac{1}{n} \sum_i^n \text{Tones}_i \times \text{Tones}_i$$

$$\langle CSWA^2 \rangle = \frac{1}{n} \sum_i^n CSWA_i \times CSWA_i$$

In some embodiments, n may be a number of initial sleep sessions for which initial model 518 must receive data before generating personalized model 512. In some embodiments, for calculations of the initial sleep sessions, the boost values in equations 1 and 2 are baseline boost values (i.e., baseline boost 506), which relate to the matched population.

As shown in system 500, personalized boost 514 may be combined with baseline boost 506 to generate boost 508. In some embodiments, system 500 may use equation 3 and/or other equations to calculate boost 508.

$$\text{Boost} = (1-\lambda) \times \text{baseline boost} + \lambda \times \text{personalized boost} \quad \text{Equation 3:}$$

In some embodiments, lambda may be a constant between zero and one. In some embodiments, lambda controls the relative importance of baseline boost and personalized boost to overall boost. In some embodiments, lambda may be a variable. For example, the system may initially use a small value of lambda (e.g., 0.1) in order to increase the relative importance of baseline boost for an initial number of sleep sessions. Thereafter, the system may increase the value of lambda such that the personalized boost plays an increasingly important role in calculating overall boost. In some embodiments, boost 508 may be used for boost calculation 412, as shown in FIG. 4.

In some embodiments, coefficients $\beta_0$, $\beta_1$, and $\beta_2$ may be empirically estimated with available data and may be continuously updated as new data becomes available. In some embodiments, system 500 may use equation 4 and/or other equations to continuously update the calculations above.

$$\text{Personalized Boost}_{n+1} = \beta_0 + \beta_1 \times \text{Tones}_{n+1}$$

$$\text{Boost}_{n+1} = (1-\lambda) \times \text{baseline boost}_{n+1} + \lambda \times \text{personalized boost}_{n+1} \quad \text{Equation 4:}$$

Once data is available for a subsequent sleep session (i.e., each sleep session after the initial sleep sessions), system 500 must update equation 2. In some embodiments, system 500 may use equation 5 and/or other equations to update equation 2.

$$\langle \text{Tones} \rangle = (1-\theta) \times \langle \text{Tones} \rangle + \theta \times \text{Tones}_{n+1}$$

$$\langle CSWA \rangle = (1-\theta) \times \langle CSWA \rangle + \theta \times CSWA_{n+1}$$

$$\langle \text{Boost} \rangle = (1-\theta) \times \langle \text{Boost} \rangle + \theta \times \text{Boost}_{n+1}$$

$$\langle \text{Tones} \times \text{Boost} \rangle = (1-\theta) \times \langle \text{Tones} \times \text{Boost} \rangle + \theta \times \text{Tones}_{n+1} \times \text{Boost}_{n+1}$$

$$\langle CSWA \times \text{Boost} \rangle = (1-\theta) \times \langle CSWA \times \text{Boost} \rangle + \theta \times CSWA_{n+1} \times \text{Boost}_{n+1}$$

$$\langle \text{Tones} \times \text{CSWA} \rangle = (1-\theta) \times \langle \text{Tones} \times \text{CSWA} \rangle + \theta \times \text{Tones}_{n+1} \times \text{CSWA}_{n+1}$$

$$\langle \text{Tones}^2 \rangle = (1-\theta) \times \langle \text{Tones}^2 \rangle + \theta \times \text{Tones}_{n+1} \times \text{Tones}_{n+1}$$

$$\langle \text{CSWA}^2 \rangle = (1-\theta) \times \text{CSWA} + \theta \times \text{CSWA}_{n+1} \times \text{CSWA}_{n+1} \quad \text{Equation 5:}$$

In some embodiments, θ is a constant between zero and one which controls the influence of the new data on the updating of personalized model 512. For example, a higher value of θ leads to a higher influence of the updating of personalized model 512. In some embodiments, a default value of θ may be 0.1 (e.g., if there are approximately ten valid sleep sessions factored into equation 2). In some embodiments, the value of θ and/or the number of valid sleep sessions factored into equation 2 may vary.

Returning to FIG. 4, in some embodiments, for sleep sessions falling within the initial sleep sessions, any sleep quality feedback delivered to the subject may utilize baseline boost 506 for boost calculation 412. In some embodiments, for sleep sessions that occur after the initial sleep sessions, system 400 may utilize boost 508, which includes boost information for the matched population as well as information specific to the subject, for boost calculation 412.

In some embodiments, the sleep quality feedback score 418 is calculated for each sleep session of the subject. In some embodiments, sleep quality feedback score 418 is calculated for several sleep sessions of the subject. In some embodiments, sleep quality feedback score 418 represents the subject's sleep quality over time and may be updated with information from each new sleep session. In some embodiments, sleep quality feedback score 418 is provided to the subject after each sleep session. Sleep quality feedback score 418 may be provided to the subject via the same device that is used to provide sensory stimulation to the subject (e.g., headset 201, as shown in FIG. 2). In some embodiments, sleep quality feedback score 418 is provided to the subject via a separate application (e.g., on a mobile phone, tablet, computer, etc.). In some embodiments, sleep quality feedback score 418 may be delivered to the subject as a message (e.g., via text message or email). Sleep quality feedback score 418 may be provided to the subject using any combination of the aforementioned methods and/or other methods.

In some embodiments, the one or more processors (e.g., 20, as shown in FIG. 1) may be configured to control the one or more sensory stimulators (e.g., 16, as shown in FIG. 1) based on baseline model 504 and updated personalized model 512. For example, if sleep feedback score 418 indicates poor sleep quality, the one or more processors may adjust stimulation parameters (e.g., by increasing the intensity) for the sensory stimulation. The sensory stimulators may then deliver the sensory stimulation to the subject (e.g., in a subsequent sleep session) according to the adjusted stimulation parameters.

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), cloud storage, and/or other electronically readable storage media. Electronic storage 22 may store software algorithms, information determined by processor 20, information received via subject interface 24 and/or external computing systems (e.g., external resources 18), and/or other information that enables system 10 to function as described herein. Electronic storage 22 may be (in whole or in part) a separate component within system 10, or electronic storage 22 may be provided (in whole or in part) integrally with one or more other components of system 10 (e.g., processor 20).

Subject interface 24 is configured to provide an interface between system 10 and subject 12, and/or other subjects through which subject 12 and/or other subjects may provide information to and receive information from system 10. This enables data, cues, results, and/or instructions and any other communicable items, collectively referred to as "information," to be communicated between a subject (e.g., subject 12) and one or more of sensor 14, sensory stimulator 16, external resources 18, processor 20, and/or other components of system 10. For example, a hypnogram, EEG data, deep sleep stage probability, and/or other information may be displayed for subject 12 or other subjects via subject interface 24. As another example, subject interface 24 may be and/or be included in a computing device such as a desktop computer, a laptop computer, a smartphone, a tablet computer, and/or other computing devices. Such computing devices may run one or more electronic applications having graphical subject interfaces configured to provide information to and/or receive information from subjects.

Examples of interface devices suitable for inclusion in subject interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, subject interface 24 comprises a plurality of separate interfaces. In some embodiments, subject interface 24 comprises at least one interface that is provided integrally with processor 20 and/or other components of system 10. In some embodiments, subject interface 24 is configured to communicate wirelessly with processor 20 and/or other components of system 10.

It is to be understood that other communication techniques, either hard-wired or wireless, are also contemplated by the present disclosure as subject interface 24. For example, the present disclosure contemplates that subject interface 24 may be integrated with a removable storage interface provided by electronic storage 22. In this example, information may be loaded into system 10 from removable storage (e.g., a smart card, a flash drive, a removable disk, etc.) that enables the subject(s) to customize the implementation of system 10. Other exemplary input devices and techniques adapted for use with system 10 as subject interface 24 comprise, but are not limited to, an RS-232 port, RF link, an IR link, modem (telephone, cable or other). In short, any technique for communicating information with system 10 is contemplated by the present disclosure as subject interface 24.

Figure 6:
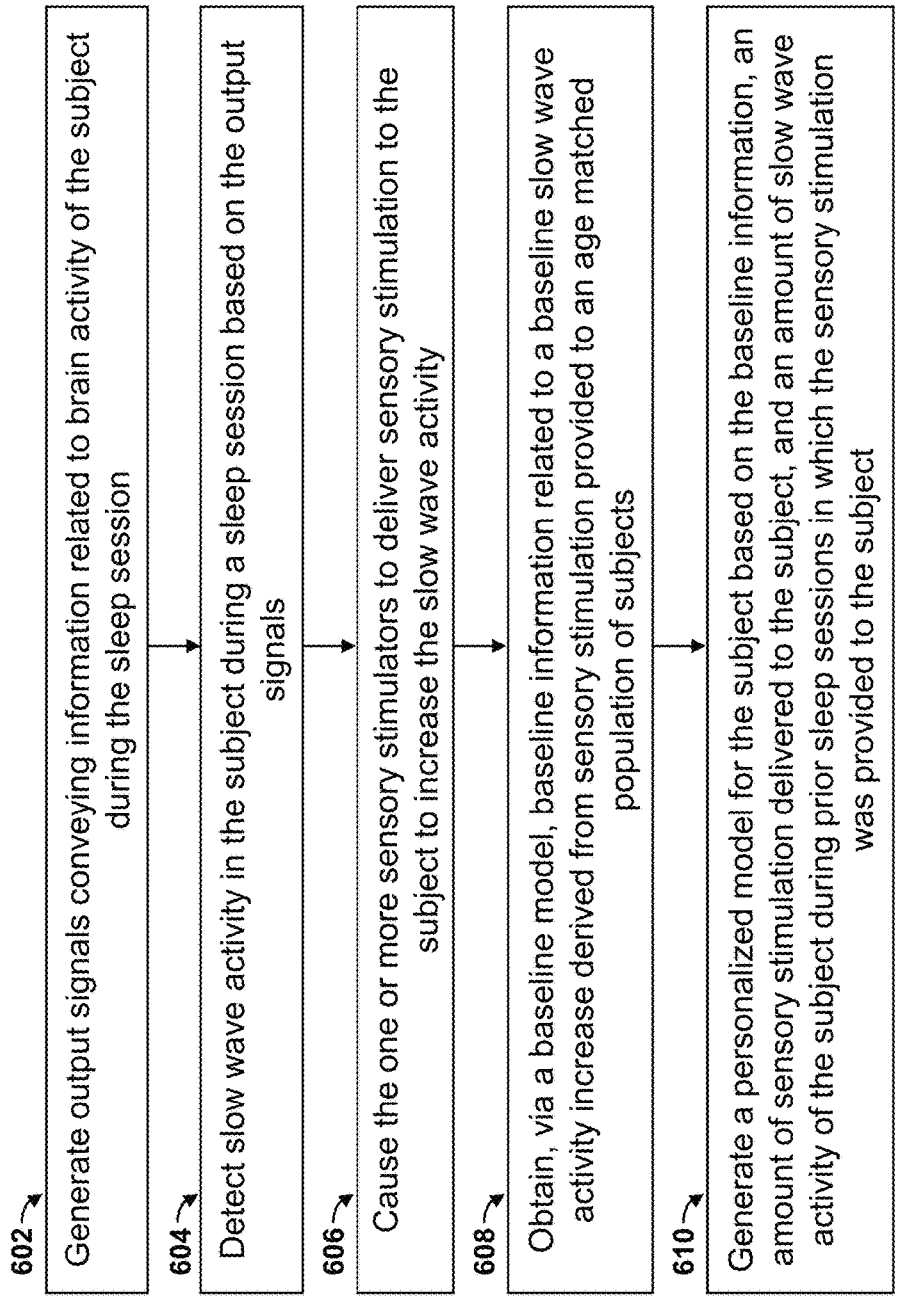
FIG. 6 illustrates a method for measuring slow wave activity of a subject during a sleep session, in accordance with one or more embodiments.

FIG. 6 illustrates method 600 for measuring slow wave activity of a subject during a sleep session. The system comprises one or more sensors, one or more sensory stimulators, one or more processors configured by machine-readable instructions, and/or other components. The one or more processors are configured to execute computer program components. The computer program components comprise an information component, a model component, a control component, a modulation component, and/or other components. The operations of method 600 presented below are intended to be illustrative. In some embodiments, method 600 may be accomplished with one or more additional operations not described, and/or without one or more of the operations discussed. Additionally, the order in which the operations of method 600 are illustrated in FIG. 6 and described below is not intended to be limiting.

In some embodiments, method 600 may be implemented in one or more processing devices such as one or more processors 20 described herein (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 600 in response to instructions stored electronically on an electronic storage medium. The one or more processing devices may include one or more devices configured through hardware, firmware, and/or software to be specifically designed for execution of one or more of the operations of method 600.

At an operation 602, output signals conveying information related to brain activity of the subject during the sleep session are generated. The output signals are generated during a sleep session of the subject and/or at other times. In some embodiments, operation 602 is performed by sensors the same as or similar to sensors 14 (shown in FIG. 1 and described herein).

In some embodiments, operation 602 includes providing the information in the output signals to the deep learning algorithm in temporal sets that correspond to individual periods of time during the sleep session. In some embodiments, operation 602 includes causing the trained deep learning algorithm to output the detected deep sleep for the subject during the sleep session based on the temporal sets of information. In some embodiments, operation 602 is performed by a processor component the same as or similar to model component 32 (shown in FIG. 1 and described herein).

At an operation 604, slow wave activity is detected in the subject during a sleep session based on the output signals. In some embodiments, the slow wave activity indicates a sleep stage (e.g., N3, N2, N1, REM, or wakefulness). If the slow wave activity of the subject indicates deep sleep (e.g., N3 sleep stage), the one or more processors may control the one or more sensory stimulators to provide sensory stimulation to the subject during the deep sleep. In some embodiments, the one or more processors may determine that the subject has been in deep sleep for a threshold amount of time before controlling the sensory stimulators to provide sensory stimulation. In some embodiments, the one or more processors may determine that the likelihood of microarousals is below a threshold before controlling the sensory stimulators to provide sensory stimulation. In some embodiments, operation 604 is performed by a processor component the same as or similar to control component 34 (shown in FIG. 1 and described herein).

At an operation 606, sensory stimulation is delivered to the subject to increase the slow wave activity. In some embodiments, the sensory stimulation may be in the form of auditory vibrations, haptic vibrations, light pulses, and/or another type of sensory stimulation. In some embodiments, the sensory stimulation may be provided to the subject as repeating stimulations with a constant interval between stimulations and/or constant stimulations. In some embodiments, the sensory stimulators may vary the intensity of the stimulations based on the depth of sleep (e.g., as detected by the one or more sensors). In some embodiments, the parameters (e.g., amount, timing, intensity, etc.) may be modulated by the sensory stimulators (e.g., 16, as shown in FIG. 1). In some embodiments, operation 606 is performed by a processor component the same as or similar to modulation component 36 (shown in FIG. 1 and described herein).

At an operation 608, baseline information is obtained via a baseline model, wherein the baseline information is related to a baseline slow wave activity increase derived from sensory stimulation provided to an age matched population of subject. The baseline information may comprise information about increases in the slow wave activity during deep sleep for different age ranges as a function of sensory stimulation provided to the age matched population of subjects. In some embodiments, the information related to increases in slow wave activity in the age matched population of subjects is received or preprogrammed. The system may select the age group that corresponds to the subject. In some embodiments, operation 608 is performed by a processor component the same as or similar to control component 34 (shown in FIG. 1 and described herein).

At an operation 610, a personalized model is generated, where the personalized model is based on the baseline information obtained via the baseline model, an amount of sensory stimulation delivered to the subject, and an amount of slow wave activity of the subject during prior sleep sessions in which sensory stimulation was provided to the subject. In some embodiments, the personalized model is configured to provide personalized information related to a slow wave activity increase derived from the sensory stimulation provided to the subject. In some embodiments, operation 610 is performed by a processor component the same as or similar to control component 34 (shown in FIG. 1 and described herein.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to measure slow wave activity during a sleep session, the system comprising:
   one or more electroencephalogram sensors;
   one or more sensory stimulators configured to provide first auditory tones to a subject; and
   one or more processors coupled to the one or more electroencephalogram sensors and the one or more sensory stimulators, the one or more processors configured by machine-readable instructions to:
detect, via the one or more electroencephalogram sensors, slow wave activity of the subject during a sleep session; and
control, based on the detection of the slow wave activity, the one or more sensory stimulators to deliver the first auditory tones to the subject to increase the slow wave activity, each of the first auditory tones being less than one decisecond in length;
obtain, via a baseline model, baseline information related to a baseline slow wave activity increase throughout deep sleep as a function of second auditory tones provided to an age matched population of subjects, wherein the baseline model is configured to provide the baseline information based on a cumulative number of the second auditory tones delivered to the age matched population; and
generate a personalized model for the subject based on (i) the baseline information, wherein the baseline information is used as an approximation of slow wave activity of the subject during the sleep session, (ii) a cumulative number of the first auditory tones delivered to the subject, and (iii) a cumulative amount of slow wave activity of the subject during prior sleep sessions in which the first auditory tones were provided to the subject, such that the personalized model is configured to provide personalized information related to a personalized slow wave activity increase derived from the first auditory tones provided to the subject.

2. A system configured to measure slow wave activity during a sleep session, the system comprising:
one or more sensors configured to generate output signals conveying information related to brain activity of a subject during a sleep session;
one or more sensory stimulators configured to provide first sensory stimulation to the subject; and
one or more processors coupled to the one or more sensors and the one or more sensory stimulators, the one or more processors configured by machine-readable instructions to:
detect, based on the output signals, slow wave activity of the subject during a sleep session; and
cause, based on the detection of the slow wave activity, the one or more sensory stimulators to deliver the first sensory stimulation to the subject to increase the slow wave activity;
obtain, via a baseline model, baseline information related to a baseline slow wave activity increase throughout deep sleep as a function of second sensory stimulation provided to an age matched population of subjects; and
generate a personalized model for the subject based on (i) the baseline information, wherein the baseline information is used as an approximation of slow wave activity of the subject during the sleep session, (ii) a cumulative amount of the first sensory stimulation delivered to the subject, and (iii) a cumulative amount of slow wave activity of the subject during prior sleep sessions in which the first sensory stimulation was provided to the subject, such that the personalized model is configured to provide personalized information related to a personalized slow wave activity increase derived from the first sensory stimulation provided to the subject.

3. The system of claim 2, wherein the baseline model comprises sleep architecture information, second sensory stimulation information, and cumulative slow wave activity information for the age matched population of subjects.

4. The system of claim 2, wherein the slow wave activity of the subject during the sleep session indicates deep sleep.

5. The system of claim 2, wherein the one or more processors are further configured to:
detect, based on the output signals, slow wave activity of the subject during a plurality of initial sleep sessions;
store information related to the baseline slow wave activity increase of the age matched population of subjects; and
generate an initial model describing initial slow wave activity increases of the subject based on the stored information and the slow wave activity of the subject during the plurality of initial sleep sessions.

6. The system of claim 5, wherein the information related to the baseline slow wave activity increase of the age matched population of subjects is received or preprogrammed.

7. The system of claim 5, wherein the one or more processors are further configured to provide sleep quality feedback to the subject following the plurality of initial sleep sessions based on the baseline model.

8. The system of claim 5, wherein the one or more processors are further configured to generate the personalized model based on the initial model.

9. The system of claim 2, wherein the one or more processors are further configured to modify the personalized model based on the baseline model and the slow wave activity measured by the one or more sensors during the sleep session.

10. The system of claim 9, wherein the one or more processors are further configured to provide sleep quality feedback to the subject following the sleep session based on the baseline model and the modified personalized model.

11. The system of claim 9, wherein the one or more processors are further configured to determine a personalized slow wave activity increase of the subject in a subsequent sleep session based on the baseline model and the modified personalized model.

12. A method for measuring slow wave activity during a sleep session with a system, the system comprising one or more sensors, one or more sensory stimulators, and one or more processors, the method comprising:
generating, with the one or more sensors, output signals conveying information related to brain activity of a subject during the sleep session;
detecting, with the one or more processors, slow wave activity of the subject during a sleep session based on the output signals; and
causing, based on the detection of the slow wave activity, the one or more sensory stimulators to deliver first sensory stimulation to the subject to increase the slow wave activity;
obtaining, via a baseline model, baseline information related to a baseline slow wave activity increase throughout deep sleep as a function of second sensory stimulation provided to an age matched population of subjects; and
generating a personalized model for the subject based on (i) the baseline information, wherein the baseline information is used as an approximation of slow wave activity of the subject during the sleep session, (ii) a cumulative amount of the first sensory stimulation delivered to the subject, and (iii) a cumulative amount of slow wave activity of the subject during prior sleep sessions in which the first sensory stimulation was provided to the subject, such that the personalized model is configured to provide personalized information related to a personalized slow wave activity increase derived from the first sensory stimulation provided to the subject.

13. The method of claim 12, wherein the baseline model comprises sleep architecture information, second sensory stimulation information, and cumulative slow wave activity information for the age matched population of subjects.

14. The method of claim 12, wherein the slow wave activity of the subject during the sleep session indicates deep sleep.

15. The method of claim 12, further comprising:
detecting, with the one or more processors, based on the output signals, slow wave activity of the subject during a plurality of initial sleep sessions;
storing, with the one or more processors, information related to the baseline slow wave activity increase of the age matched population of subjects; and
generating, with the one or more processors, an initial model describing initial slow wave activity increases of the subject based on the stored information and the slow wave activity of the subject during the plurality of initial sleep sessions.

16. The method of claim 15, wherein the information related to the baseline slow wave activity increase of the age matched population of subjects is received or preprogrammed.

17. The method of claim 15, further comprising providing sleep quality feedback to the subject following the plurality of initial sleep sessions based on the baseline model.

18. The method of claim 15, further comprising generating the personalized model based on the initial model.

19. The method of claim 12, further comprising modifying the personalized model based on the baseline model and the slow wave activity measured by the one or more sensors during the sleep session.

20. The method of claim 19, further comprising providing sleep quality feedback to the subject following the sleep session based on the baseline model and the modified personalized model.

21. The method of claim 19, further comprising determining a personalized slow wave activity increase of the subject in a subsequent sleep session based on the baseline model and the modified personalized model.

* * * * *